(12) United States Patent
Karhi

(10) Patent No.: US 7,159,344 B2
(45) Date of Patent: Jan. 9, 2007

(54) PLOW MOLDBOARD ASSEMBLY HAVING MULTIPLE GROUND ENGAGING BLADES

(75) Inventor: Kevin Karhi, Desbarats (CA)

(73) Assignee: Inverta Corp., Desbarats (CA)

( * ) Notice: Subject to any disclaimer, the term of this patent is extended or adjusted under 35 U.S.C. 154(b) by 133 days.

(21) Appl. No.: 10/912,204

(22) Filed: Aug. 6, 2004

(65) Prior Publication Data

US 2006/0026870 A1 Feb. 9, 2006

(51) Int. Cl.
*E02F 9/28* (2006.01)

(52) U.S. Cl. .......................... 37/449; 37/266; 37/232; 172/811

(58) Field of Classification Search ................ 37/266, 37/270, 232, 233, 264, 446, 449; 172/811, 172/817
See application file for complete search history.

(56) References Cited

U.S. PATENT DOCUMENTS

| | | | | |
|---|---|---|---|---|
| 3,160,967 A | * | 12/1964 | Nichols | 37/446 |
| 3,520,076 A | * | 7/1970 | Nichols | 37/446 |
| 3,529,677 A | | 9/1970 | Stephenson | |
| 3,665,623 A | * | 5/1972 | White | 37/458 |
| 3,684,032 A | | 8/1972 | Hawkins | |
| 3,685,177 A | * | 8/1972 | Hahn et al. | 37/446 |
| 3,736,664 A | * | 6/1973 | Black et al. | 37/446 |
| 3,864,853 A | * | 2/1975 | Klett et al. | 37/446 |
| 3,888,027 A | | 6/1975 | Toews | |
| 3,984,929 A | | 10/1976 | Meyer et al. | |
| 4,058,173 A | | 11/1977 | Carson | |
| 4,346,528 A | | 8/1982 | Shwayder | |
| 4,414,764 A | * | 11/1983 | Johansson et al. | 37/450 |
| 4,501,079 A | * | 2/1985 | Hahn et al. | 37/450 |
| 5,224,555 A | | 7/1993 | Bain et al. | |
| 5,778,572 A | | 7/1998 | Lukavich et al. | |

* cited by examiner

*Primary Examiner*—Thomas A Beach
(74) *Attorney, Agent, or Firm*—Trevor C. Klotz

(57) ABSTRACT

A plow moldboard assembly having multiple ground engaging blades is provided with a plurality of elongate blade receiving slots having an open top and an open bottom and each defined by front and rear walls and two end walls disposed rearward of the rear major face of the moldboard and which extend along the bottom edge of the moldboard. A plurality of ground engaging blades are arranged in side-by-side relationship, each one having front and rear blade faces and upper and lower blade portions. The front face of the lower portion is forwardly offset relative to the front face of the upper rectangular portion such that the upper rectangular portion is received in the slot and held in position by detachable securing means. Damaged blades, which are relatively light in weight can be individually removed from the elongate slot and replaced with an undamaged blade. If desired, the front and rear faces of all of the blades can collectively be reversed thereby extending the life of each blade.

6 Claims, 3 Drawing Sheets

PLOW MOLDBOARD ASSEMBLY HAVING MULTIPLE GROUND ENGAGING BLADES

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING

Not Applicable

BACKGROUND OF THE INVENTION

The subject invention generally relates to a plow assembly of the type comprising a moldboard with one or more ground engaging blades detachably secured to the moldboard and which are located along and below its bottom edge.

Plow moldboards such as those used in earth removal or snow plowing operations are typically constructed with one or more replaceable ground engaging blades which are commonly made out of hardened steel.

Blades as used on conventional snowplows normally have an 11 foot long steel backing or moldboard with three, 44 inch carbide blades bolted to it. These blades are very heavy (approximately 150 pounds for a steel backing and 75 pounds for each carbide section) and are susceptible to a short wear life due to their ongoing abrasive wear with the ground. Blade replacement can be time consuming particularly where the attachment bolts are bent or frozen, and also relatively dangerous due to their weight.

BRIEF SUMMARY OF THE INVENTION

This invention is directed towards a plow assembly of the type comprising a moldboard and a plurality of ground engaging blades which are detachably secured to the moldboard and arranged in side-by-side relationship along and below the bottom edge of the moldboard.

In accordance with one aspect of this invention, the moldboard which has front and rear major faces and an elongate bottom edge, is provided with an elongate blade receiving slot defined by rear and front walls and two end walls that is disposed rearward of the rear major face of the moldboard and which extends along the bottom edge of the moldboard. A plurality of ground engaging blades are provided, each one having a generally solid rectangular configuration with front and rear blade faces and upper and lower rectangular blade portions, and which are detachably secured to the moldboard in side-by-side relationships. The front face of the lower portion is forwardly offset relative to the front face of the upper rectangular portion such that the upper rectangular portion is received in the slot and held in that position by the detachable securing means. Further, because the front face of the lower portion is forwardly offset relative to the front face of the upper rectangular portion, it can advantageously lie in a plane flush with the front major face of the moldboard.

In accordance with another feature of this invention, the forward offset between the front faces of the upper and lower rectangular portions of each blade can comprise a front ledge between the two and which abuts an undersurface of the elongate bottom edge of the moldboard. This feature effectively distributes any upwardly directed impact experienced by a given blade to the moldboard along the surface of the front ledge, thereby reducing the impact force which would otherwise be applied to the means which detachably secures the blade to the moldboard, such as a nut and bolt or locking pin arrangement.

In order to better distribute the vertical and/or rearwardly directed impacts or blows experienced by a given blade, in a like fashion, the rear face of the lower rectangular section can be rearwardly offset relative to the rear face of the upper rectangular section along a rear ledge. Since the rear ledge is designed to abut a bottom portion of the rear wall forming the elongate slot, impacts are translated to the moldboard along the ledge rather than simply at the bolt or pin connection of the blade to the moldboard.

In order to minimize free play between the upper rectangular portion which is located within the slot, its thickness should generally correspond to the width of the slot. The slot itself is preferably also open along the top of its elongate extent so that should a damaged blade require removal and be physically jammed within the slot, it can be accessed from the open top portion of the slot for the purpose of driving it out in a downward direction.

Preferably, the upper rectangular portion of each blade is disposed centrally over its lower rectangular portion, thereby facilitating the above described front and rear ledges. Additionally, the width of the upper rectangular portion can be shorter than the width of the lower rectangular portion so that a gap is created between the upper rectangular portions of adjacent ground engaging blades. By employing gaps of this nature, within the elongate slot, a row of in-line sub-slots can be created and separated by a series of transverse walls extending between the front and rear walls of the elongate slot. In this arrangement, the upper rectangular portion of each blade and more particularly its front and rear faces and sidewalls are contained within the interior sidewalls of the sub-slots and which inpart added support to the blade located therein.

In order to add additional support to adjacent blades, in another preferred form of this invention, the sidewalls of adjacent lower rectangular blade portions can overlap one another such that a frontal impact experience by a given blade is not absorbed entirely by that blade but rather at least in part communicated over to its overlapping and neighbouring blade. In a preferred arrangement, the sidewalls of adjacent lower blade portions overlap in a tongue-and-groove manner.

DETAILED DESCRIPTION OF THE DRAWINGS

While the plow assembly of my invention has application to and can be used in earth moving or grading operations, the assembly illustrated in FIGS. 1 through 6 is directed towards a plow assembly as may be used in snow removal operations.

As illustrated, the snow plow assembly comprises curved moldboard 1, having front and rear major faces 2 and 3 as well as top edge 4 and bottom edge 5 as is well known in the art.

Figure 1:
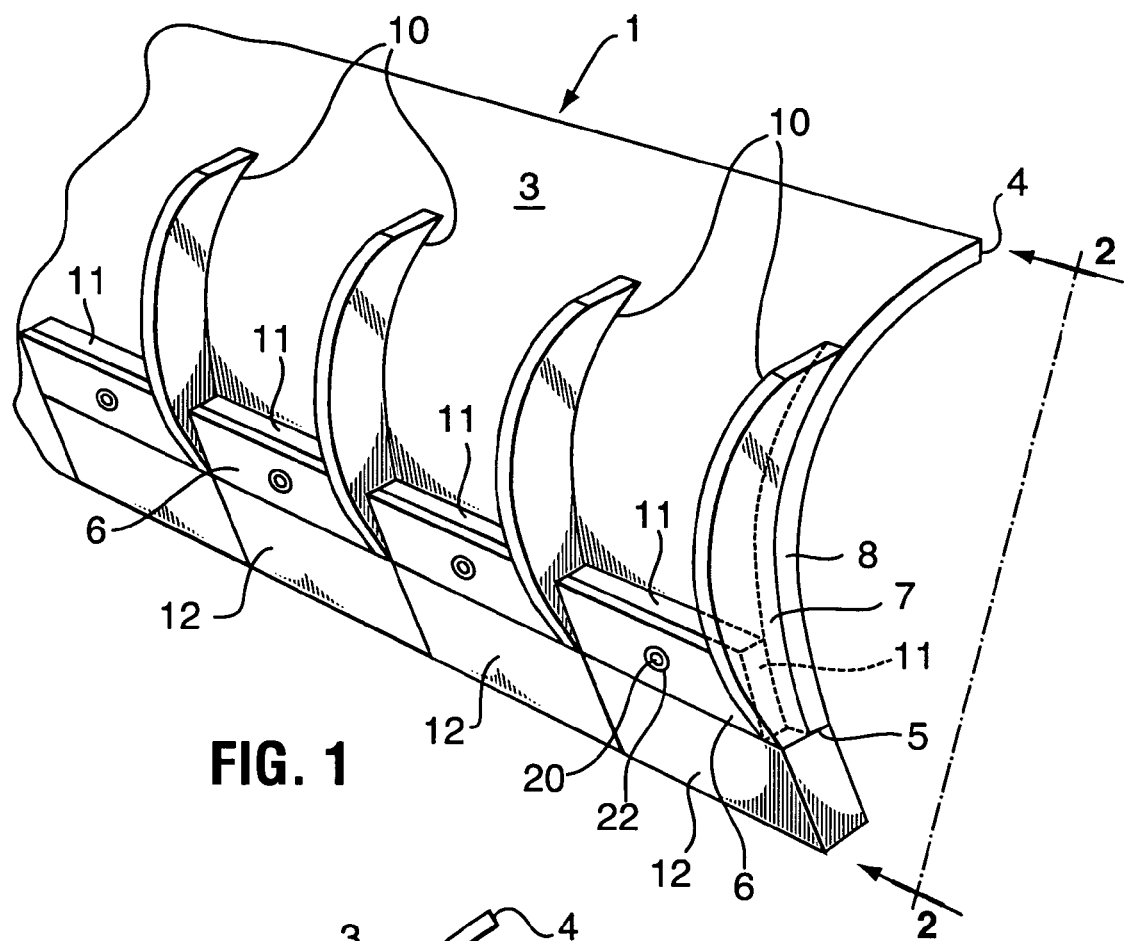
FIG. 1 is a fragmentary rear perspective view of the moldboard and ground engaging blades embodying principles of this invention.
Figure 2:
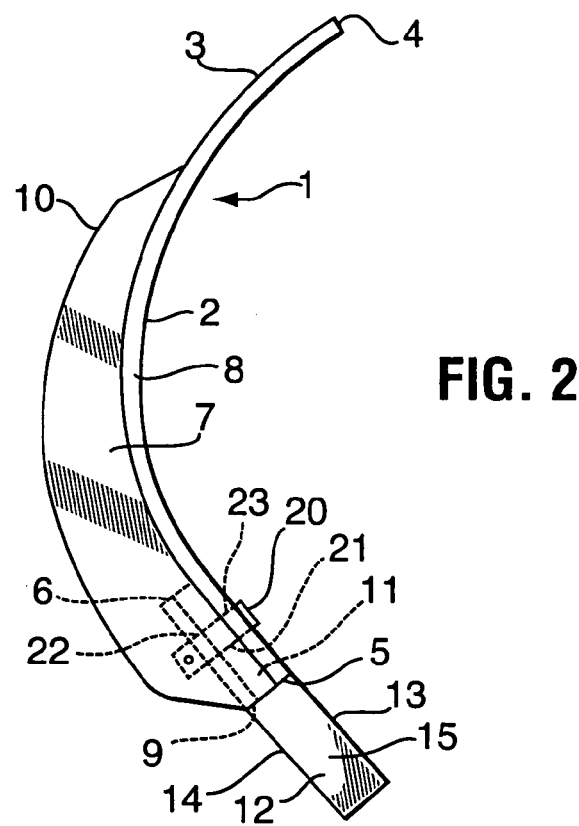
FIG. 2 is a side elevation of the moldboard and blade assembly taken along the lines 2—2 of FIG. 1.

As best seen in FIG. 1, an elongate blade receiving slot is formed from a rear wall in the form of an elongate bar 6, a front wall which in this instance is made up from the lower portion of the rear major face 3, and a pair of end walls 7 adjacent to ends 8 of moldboard 1 (only one of end wall 7 and moldboard end 8 being shows in FIGS. 1 and 2).

As is also well known in the art, rear face 3 of moldboard 1, which itself can be made up from a single or multiple pieces of metal welded together (not shown), is provided with a plurality of spaced apart reinforcing ribs 10. For reasons which will be apparent from that which follows, ribs 10 can advantageously extend interiorly of the elongate slot between elongate bar 6 and rear face 3 and welded thereto in a known manner. As will also be apparent, ribs 10 including the rib forming the end walls 7 of the elongate slot effectively create a series of inline sub-slots or cavities therebetween, which each receive rectangular upper portion 11 of detachable blades 12.

Referring now to FIGS. 3 through 6, each ground engaging blade 12 is of generally solid rectangular configuration, having front and rear blade faces 13 and 14, upper rectangular portion 11, and lower rectangular portion 15. The front face 13 of lower portion 15 is forwardly offset relative to upper portion 11 along front ledge 17. In a like manner, on the rear blade face 14, rear ledge 18 is created between rearwardly offset lower portion 15 and upper portion 11.

As also seen in FIGS. 3 through 6, a spacing or gap exists between upper portions 11 of adjacent blades 12 and which spacing is slightly larger than the thickness of ribs 10 seen in FIG. 1. As noted above and again with reference to FIG. 1, upper portions 11 of blades 12 are respectively received in the sub-slots defined between opposed ribs 10, elongate bar 6 and rear face 3 of moldboard 1. Each blade is held in location within a sub slot by means of locking connectors such as locking pins 20 which extend through apertures 21 in blades 12 as well as corresponding inline apertures 22 and 23 respectively located in the elongate bar 6 and moldboard.

Figure 3:
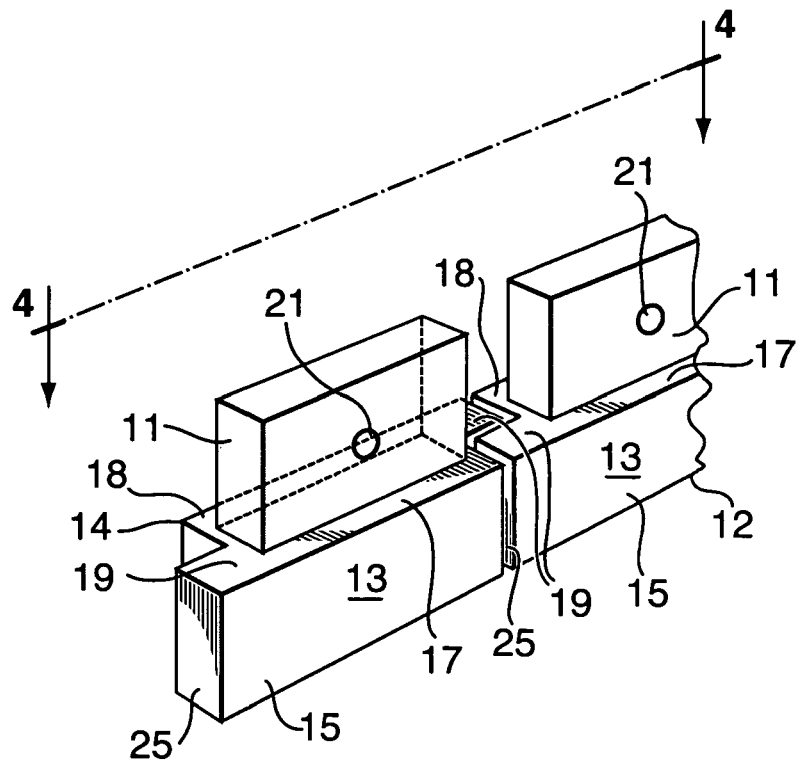
FIG. 3 is an enlarged perspective view of adjacent ground engaging blades which are identical to one another and wherein a gap is created between the upper rectangular portions of adjacent blades and which also illustrate the overlapping sidewalls of the lower rectangular portions of the blade.
Figure 4:
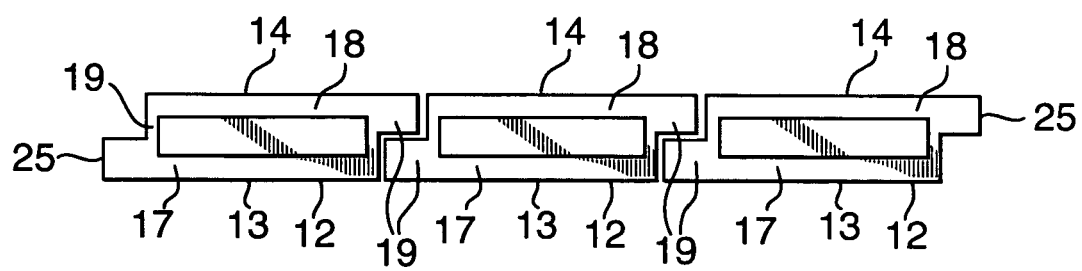
FIG. 4 is a top plan view of the adjacent ground engaging blades taken along the lines 4—4 of FIG. 3.

In order to better distribute impact forces experienced by any one of blades 12 during plow operations, and as seen in FIGS. 3 and 4, the sidewalls 25 of the lower portion 15 of identically shaped blades 12 can be stepped so that adjacent ones inter-engage and thereby provide some lateral support when a blade experiences an abnormal frontal impact. Additionally, because the upper rectangular portion 11 is smaller than and centrally positioned over lower rectangular portion 15, it is effectively surrounded by front and rear ledges 17 and 18 and transverse side ledges 19. While upper rectangular portion 11 is received in the sub-slots and held in position by pin connectors 20, upwardly directed ground impacts experienced by a blade are transmitted to the remainder of the assembly as a result of ledges 17, 18 and 19 abutting the undersurface 5 of the moldboard, the undersurface 9 of elongate bar 6, and the undersurface or terminal end of rib 10, respectively.

Figure 5:
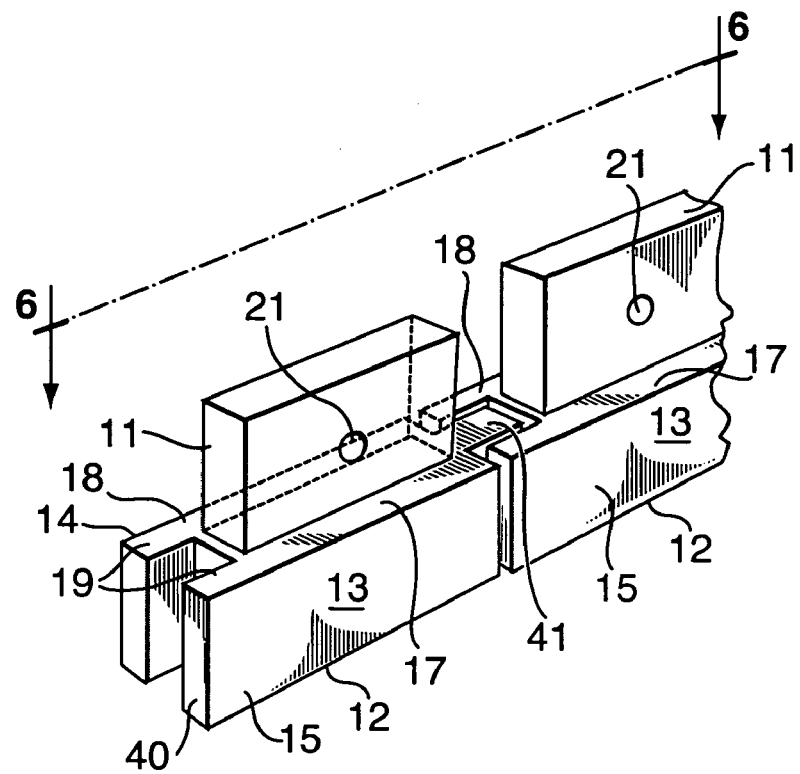
FIG. 5 is a similar view to that of FIG. 3, but where the sidewalls of lower rectangular portion of adjacent blades have a tongue and groove overlap.
Figure 6:
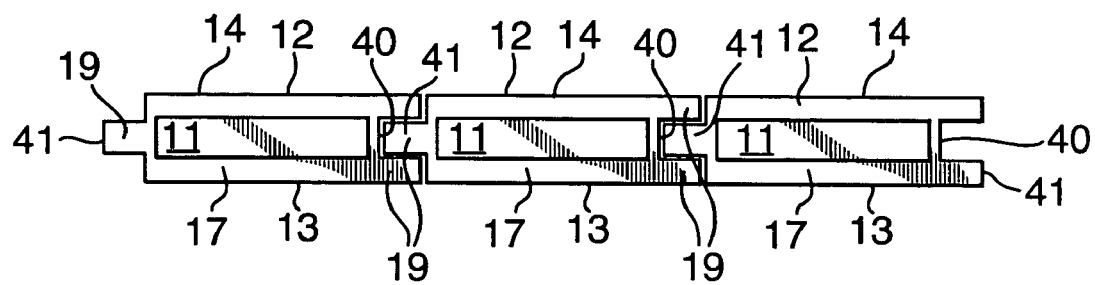
FIG. 6 is a top plan view of adjacent blades taken along the lines 6—6 of FIG. 5.

As illustrated in FIGS. 5 and 6, the sidewalls of like blades rather than being stepped, can be grooved at one end as seen at 40, and provided with a tongue 41 at the other end for a more positive interlocking between the two. However, and because each blade 12 can be identical to it's neighbouring blade, it is apparent that, if desired, the front and rear blade faces 13 and 14 can be reversed.

In the event a blade 12 becomes damaged, it can be easily removed by first withdrawing locking pin 20 from apertures 20, 21 and 21. Should upper rectangular section 11 of blade 12 become jammed in a sub-slot, because the slot is open at its top, once the pin is removed, it can be driven out of the sub-slot from the top.

Other features and advantages of this invention will be apparent from a study of the drawing, the description and the appended claims.

I claim:

1. In a plow assembly of the type comprising a moldboard having front and rear major faces and an elongate bottom edge, a plurality of ground engaging blades arranged in side-by-side relationship along and below said bottom edge, and means for detachably securing said ground engaging blades to said moldboard, the improvement comprising:

(a) a moldboard having a plurality of elongate blade receiving slots which are arranged in-line and disposed rearward of said rear major face and which extend along said bottom edge, each said slot having an open top and open bottom defined by opposed front and rear walls and two opposed side walls, and wherein said front wall comprises a portion of said rear face immediately above said bottom edge; and (b) ground engaging blades each one of which is of generally solid rectangular configuration having front and rear blade faces and upper and lower rectangular blade portions, wherein the front face of said lower portion is forwardly offset relative to the front face of said upper rectangular portion along a front ledge, wherein the rear face of said lower rectangular portion is rearwardly offset relative to the rear face of said upper rectangular portion along a rear ledge such that said upper rectangular portion of each said ground engaging blades is received in a different one of said slots, said front ledge abuts an undersurface of said elongate bottom edge, said rear ledge abuts a bottom of said rear wall, said front and rear blade faces of said ground engaging blades are reversible, and each of said ground engaging blades is held in position by said detachable securing means.

2. The plow assembly as claimed in claim 1, wherein the thickness of said upper rectangular portion corresponds to the width of each of said slots and has a thickness which is less than the thickness of said lower rectangular portion.

3. The plow assembly as claimed in claim 1, wherein said upper rectangular portion is disposed centrally over said lower rectangular portion and the length of said upper rectangular portion corresponds to the length of each of said slots and is less than the length of said lower rectangular portion.

4. The plow assembly as claimed in claim 3, wherein a gap is defined between said upper rectangular portions of adjacent ground engaging blades and one of said side walls extends through said gap.

5. The plow assembly as claimed in claim 1, wherein the upper rectangular portion of each ground engaging blade includes an aperture extending through said front and rear faces thereof and each said ground engaging blade is detachably secured to said moldboard by pin connecting means extending through said front and rear walls and said aperture.

6. The plow assembly as claimed in claim 1, wherein the sidewalls of adjacent lower rectangular blade portions are in overlapping relationship.

* * * * *